(12) United States Patent
Jungwirth et al.

(10) Patent No.: US 9,715,950 B2
(45) Date of Patent: Jul. 25, 2017

(54) SINGLE CELL APPARATUS AND METHOD FOR SINGLE ION ADDRESSING

(71) Applicant: Honeywell International Inc., Morristown, NJ (US)

(72) Inventors: Matthew Edward Lewis Jungwirth, Golden Valley, MN (US); James Goeders, Plymouth, MN (US)

(73) Assignee: Honeywell International Inc., Morris Plains, NJ (US)

( * ) Notice: Subject to any disclaimer, the term of this patent is extended or adjusted under 35 U.S.C. 154(b) by 162 days.

(21) Appl. No.: 14/686,592

(22) Filed: Apr. 14, 2015

(65) Prior Publication Data

US 2016/0307658 A1    Oct. 20, 2016

(51) Int. Cl.
*B01D 59/44*   (2006.01)
*G21K 1/00*    (2006.01)
*G01N 21/64*   (2006.01)

(52) U.S. Cl.
CPC ......... *G21K 1/003* (2013.01); *G01N 21/6452* (2013.01); *G01N 2201/067* (2013.01)

(58) Field of Classification Search
CPC ..... G01N 2201/067; G01N 2021/6484; G01N 21/6452; G01N 21/6458; G01N 21/64; G21K 1/003
USPC ........................................................ 250/281
See application file for complete search history.

(56) References Cited

U.S. PATENT DOCUMENTS

| | | | | |
|---|---|---|---|---|
| 5,527,731 A * | 6/1996 | Yamamoto | ............ | C23C 16/452 117/108 |
| 5,679,950 A * | 10/1997 | Baba | ................... | G01N 21/6404 250/281 |
| 6,462,307 B1 * | 10/2002 | Hennig | ................ | B23K 26/073 219/121.77 |
| 6,489,609 B1 * | 12/2002 | Baba | ....................... | H01J 49/42 250/281 |
| 6,516,014 B1 * | 2/2003 | Sellin | .................... | H01S 3/1303 372/18 |
| 6,753,253 B1 * | 6/2004 | Takahashi | ............. | H01J 37/304 257/E21.295 |
| 7,180,078 B2 | 2/2007 | Pau et al. | | |
| 7,447,719 B2 * | 11/2008 | Goto | ...................... | B82Y 10/00 708/191 |
| 7,826,115 B2 * | 11/2010 | Goto | ...................... | B82Y 10/00 359/108 |
| 7,859,350 B1 * | 12/2010 | Schwindt | ................ | H03L 7/099 331/3 |

(Continued)

OTHER PUBLICATIONS

Barwood, G.P., et al. "Automatic laser control for a 88Sr+ optical frequency standard", Meas. Sci. Technol. 23 (2012) 9 pp., IOP Publishing Ltd. UK & US.

(Continued)

*Primary Examiner* — David J Makiya
*Assistant Examiner* — Taeho Jo
(74) *Attorney, Agent, or Firm* — Brooks, Cameron & Huebsch, PLLC

(57) ABSTRACT

A single cell apparatus and method for single ion addressing are described herein. One apparatus includes a single cell configured to set a frequency, intensity, and a polarization of a laser, shutter the laser, align the shuttered laser to an ion in an ion trap such that the ion fluoresces light and/or performs a quantum operation, and detect the light fluoresced from the ion.

20 Claims, 1 Drawing Sheet

(56) References Cited

U.S. PATENT DOCUMENTS

| | | | | |
|---|---|---|---|---|
| 8,675,699 B2 * | 3/2014 | Dantus | G01J 11/00 | 372/25 |
| 2002/0098418 A1 * | 7/2002 | Yagi | G02F 1/0009 | 430/1 |
| 2002/0145109 A1 * | 10/2002 | Doroshenko | H01J 49/004 | 250/287 |
| 2002/0168134 A1 * | 11/2002 | Sundaram | B82Y 20/00 | 385/16 |
| 2004/0007666 A1 * | 1/2004 | Griffey | H01J 49/0077 | 250/282 |
| 2004/0011952 A1 * | 1/2004 | Johnston | G01N 27/622 | 250/287 |
| 2004/0017833 A1 * | 1/2004 | Cundiff | H01S 3/1112 | 372/18 |
| 2006/0012797 A1 * | 1/2006 | Chang | G01J 3/02 | 356/484 |
| 2006/0169914 A1 * | 8/2006 | Holle | H01J 49/164 | 250/423 P |
| 2006/0249670 A1 * | 11/2006 | Monroe | G06N 99/002 | 250/283 |
| 2007/0138386 A1 * | 6/2007 | Makarov | H01J 49/0054 | 250/288 |
| 2008/0296483 A1 * | 12/2008 | McClelland | H01J 27/24 | 250/251 |
| 2009/0084991 A1 * | 4/2009 | Ichimura | G06N 99/002 | 250/493.1 |
| 2010/0316176 A1 * | 12/2010 | Wood | G21H 1/00 | 376/190 |
| 2011/0134943 A1 * | 6/2011 | Hartl | G02F 1/365 | 372/18 |
| 2011/0238316 A1 * | 9/2011 | Ecker | C07H 21/04 | 702/19 |
| 2013/0306855 A1 * | 11/2013 | Raptakis | H01J 49/025 | 250/282 |
| 2014/0264031 A1 * | 9/2014 | Fermann | G01J 3/42 | 250/339.02 |
| 2015/0083902 A1 * | 3/2015 | Akselrod | G01N 23/22 | 250/252.1 |
| 2016/0094010 A1 * | 3/2016 | Hartl | G02F 1/365 | 372/6 |
| 2016/0118238 A1 * | 4/2016 | Gordon | H01J 49/0013 | 250/282 |

OTHER PUBLICATIONS

Brady, G.R., et al. "Integration of flourescence collection optics with a microfabricated surface electrode ion trap", Appl Phys B (2011), 103:801-808, 8 pp.

Noek, Rachel, et al., "Trapping and Cooling of 174Yb+ Ions in a Microfabricated Surface Trap", Journal of the Korean Physical Society, vol. 63, No. 4, Aug. 2013, pp. 907-913.

Search Report from related European application 16163767.3 dated Oct. 10, 2016 (11 pp.).

* cited by examiner

SINGLE CELL APPARATUS AND METHOD FOR SINGLE ION ADDRESSING

TECHNICAL FIELD

The present disclosure relates to a single cell apparatus and method for single ion addressing.

BACKGROUND

An ion trap can use a combination of electrical and magnetic fields to trap (e.g., capture) an ion (e.g., a positively or negatively charged atom or molecule). When an ion trapped in an ion trap is illuminated by a laser (e.g. when a laser beam is focused onto the ion in the trap), the ion may fluoresce light or perform a quantum operation. The light fluoresced from the ion can be detected by a detector.

Multiple ion traps can be formed on a chip (e.g., die). However, in previous approaches, each additional ion trap (e.g., each additional trapped ion) may necessitate additional structure (e.g., hardware) and/or space, including, for instance, additional lasers. For example, in previous approaches there may be a linear (e.g., one-to-one) relationship between the number of ions and the number of lasers (e.g., each additional ion may necessitate an additional laser).

Further, previous approaches may not be able to achieve single ion addressing or detecting. That is, previous approaches may not be able to individually address multiple ions such that the light fluoresced from only a single ion at a time can be detected by the detector.

DETAILED DESCRIPTION

Figure 1:
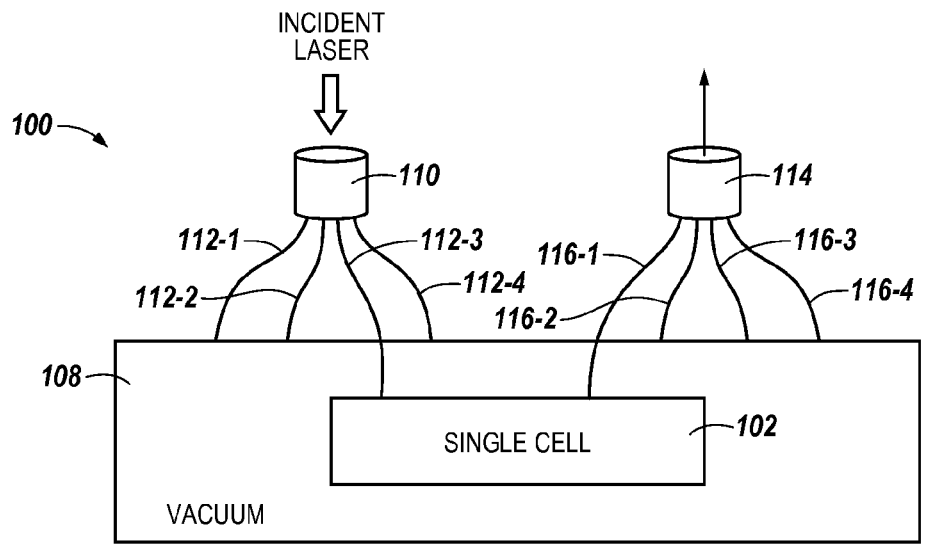
FIG. 1 illustrates an example apparatus for single ion addressing in accordance with one or embodiments of the present disclosure.

A single cell apparatus and method for single ion addressing are described herein. For example, one or more embodiments include a single cell configured to set a frequency, intensity, and a polarization of a laser, shutter the laser, align the shuttered laser to an ion in an ion trap such that the ion fluoresces light and/or performs a quantum operation, and detect the light fluoresced from the ion.

Embodiments in accordance with the present disclosure can achieve single ion addressing. That is, embodiments in accordance with the present disclosure can individually address multiple ions (e.g., ions trapped in multiple ion traps or zones of a single trap) such that the light fluoresced from only a single ion at a time can be detected by a detector.

Further, embodiments in accordance with the present disclosure may have a non-linear relationship between the number of trapped ions and the number of lasers needed for interacting with the ions. For example, in embodiments of the present disclosure, a single laser can be used to interact with multiple ions (e.g., a single laser can be used for multiple ions or ion traps).

As such, embodiments of the present disclosure can realize scalability in achieving single ion addressing. For example, embodiments of the present disclosure can achieve single ion addressing without using a significant amount of additional structure (e.g., hardware) and/or space as compared to previous approaches.

In the following detailed description, reference is made to the accompanying drawings that form a part hereof. The drawings show by way of illustration how one or more embodiments of the disclosure may be practiced.

These embodiments are described in sufficient detail to enable those of ordinary skill in the art to practice one or more embodiments of this disclosure. It is to be understood that other embodiments may be utilized and that mechanical, electrical, and/or process changes may be made without departing from the scope of the present disclosure.

As will be appreciated, elements shown in the various embodiments herein can be added, exchanged, combined, and/or eliminated so as to provide a number of additional embodiments of the present disclosure. The proportion and the relative scale of the elements provided in the figures are intended to illustrate the embodiments of the present disclosure, and should not be taken in a limiting sense.

The figures herein follow a numbering convention in which the first digit or digits correspond to the drawing figure number and the remaining digits identify an element or component in the drawing. Similar elements or components between different figures may be identified by the use of similar digits. For example, 102 may reference element "02" in FIG. 1, and a similar element may be references as 202 in FIG. 2.

As used herein, "a" or "a number of" something can refer to one or more such things. For example, "a number of lasers" can refer to one or more lasers.

FIG. 1 illustrates an example apparatus 100 for single ion addressing in accordance with one or embodiments of the present disclosure. As shown in FIG. 1, apparatus 100 can include a single (e.g., only one) cell (e.g., optical cell) 102. In the example illustrated in FIG. 1, single cell 102 is completely inside a vacuum (e.g., vacuum chamber) 108. However, in some embodiments, the single cell may be partially inside and partially outside vacuum 108 (e.g., a portion of the single cell may be inside the vacuum and a portion of the single cell may be outside the vacuum).

Single cell 102 can set a frequency, intensity, and a polarization of a laser (e.g., a laser beam), prepare the state of the laser, and shutter the laser. In some embodiments, the laser may be a Doppler cooling laser (e.g., a laser used in a Doppler cooling mechanism), and in some embodiments the laser may be a quantum operation laser (e.g., a laser used in a quantum operation, such as Raman cooling, state preparation, photoionization, loading, and/or ion transitions, for instance). In both such embodiments, the laser may be a 369 nanometer (nm) laser for a ytterbium ion. However, embodiments of the present disclosure are not limited to a particular type of laser. For example, embodiments of the present disclosure may include different types or frequencies of lasers for different types of ions or different operations.

Single cell 102 can then align the shuttered laser to (e.g., focus the shuttered laser on) an ion trapped in an ion trap for interaction with the ion to cause, for example, the ion to fluoresce (e.g., emit) light and/or perform a quantum operation. Single cell 102 can receive (e.g., collect) and detect (e.g., measure) the light fluoresced from the ion. In some embodiments, the ion in the ion trap can be a ytterbium (Yb) ion. However, embodiments of the present disclosure are not limited to a particular type of ion. Single cell 102 will be further described herein (e.g., in connection with FIG. 2).

As shown in FIG. 1, apparatus 100 can include a first fiber bundle 110 and a second fiber bundle 114. Fiber bundle 110 can split an incident laser into a plurality of components before the laser enters vacuum 108, one component of which enters single cell 102 inside vacuum 108. For instance, fiber bundle 110 can split the laser into a plurality of fibers (e.g., wires) 112-1, 112-2, 112-3, 112-4 (e.g., each laser component can propagate through a different fiber) before the laser (e.g., the laser components) enter vacuum 108, one fiber of which (e.g., fiber 112-3) enters single cell 102, as illustrated in FIG. 1. That is, the fibers split, and only a single fiber enters single cell 102, as illustrated in FIG. 1.

Although not shown in FIG. 1 for clarity and so as not to obscure embodiments of the present disclosure, each of the other respective laser components (e.g., each of the other respective fibers) can enter a different cell that is analogous to single cell 102 inside vacuum 108 (e.g., fiber 112-1 can enter a different cell that is analogous to single cell 102, fiber 112-2 can enter another different cell that is analogous to single cell 102, etc.). Alternatively, all fibers 112-1, 112-2, 112-3, and 112-4 can enter single cell 102. Further, although the embodiment illustrated in FIG. 1 includes four such fibers, embodiments of the present disclosure are not limited to a particular number of fibers.

As shown in FIG. 1, a single fiber (e.g., wire) 116-1 exits single cell 102. Fiber bundle 114 can bundle fiber 116-1 with a number of other fibers 116-2, 116-3, 116-4 after fiber 116-1 exits vacuum 108. The bundled fibers can then go to additional electronics (not shown in FIG. 1).

Although not shown in FIG. 1 for clarity and so as not to obscure embodiments of the present disclosure, each of the other respective fibers 116-2, 116-3, 116-4 may be exiting a different cell that is analogous to single cell 102 inside vacuum 108 (e.g., fiber 116-2 may be exiting a different cell that is analogous to single cell 102, fiber 116-3 may be exiting another different cell that is analogous to single cell 102, etc.). Alternatively, all fibers 116-1, 116-2, 116-3, and 116-4 can exit single cell 102. Further, although the embodiment illustrated in FIG. 1 includes four such fibers, embodiments of the present disclosure are not limited to a particular number of fibers.

Figure 2:
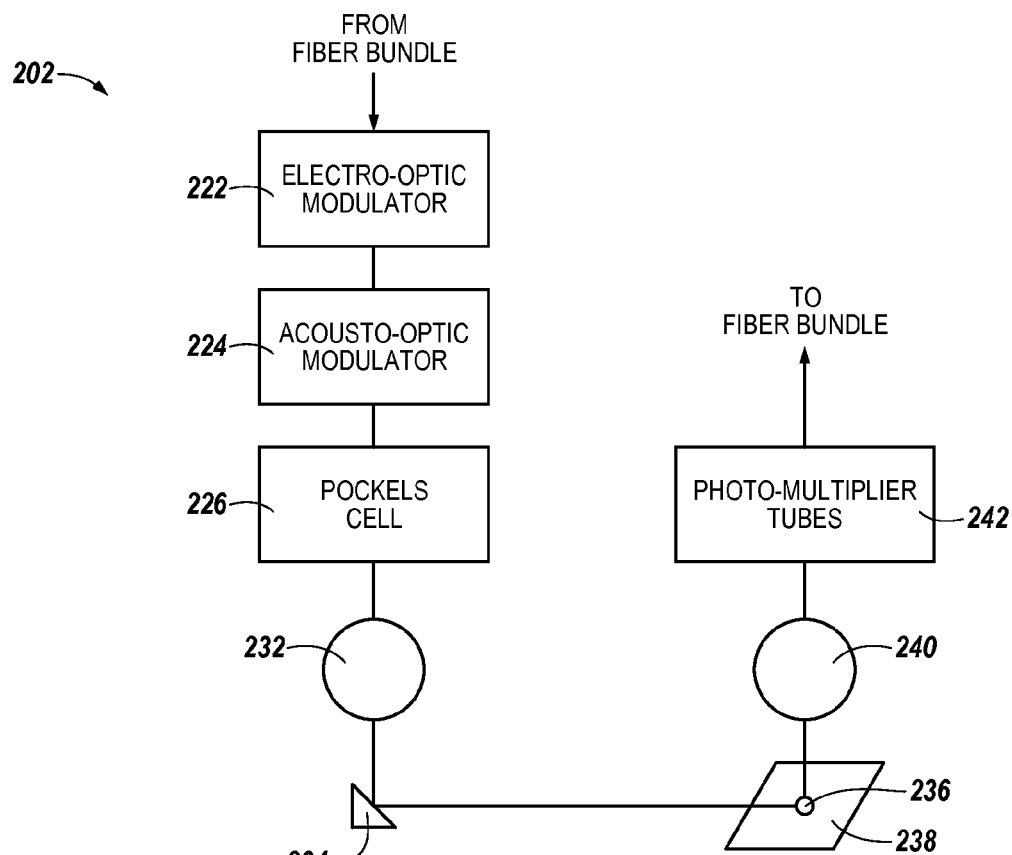
FIG. 2 illustrates a portion of a cell of an apparatus for single ion addressing in accordance with one or embodiments of the present disclosure.

The number of ions a single laser can individually address using apparatus 100 may depend on three factors: the power of the illuminating laser, the laser power needed at the ion for the desired interaction, and the loss caused by the components within cell 102 that set the frequency, intensity, and polarization of the laser, shutter the laser, and prepare the state of the laser (e.g., the electro-optic modulator (EOM), the acousto-optic modulator (AOM), and the Pockels cell described in connection with FIG. 2). For example, the total transmission $T_{tot}$ in cell 102 can be given by:

$$T_{tot}=T_{EOM}T_{AOM}T_{Pockels}=0.3*0.7*0.99=0.2$$

where $T_{EOM}$, $T_{AOM}$, and $T_{Pockels}$ are the estimated transmissions of the EOM, AOM, and Pockels cell, respectively. The power at the ion $\Phi_{ion}$ can then be given by:

$$\Phi_{ion}=T_{tot}T_{laser}=0.2*\Phi_{laser}$$

where $\Phi_{laser}$ is the power of the laser. The number of ions N that the laser can individually address can be given by:

$$N=\Phi_{ion}/\Phi_{required}=(0.2*\Phi_{laser})/\Phi_{required}$$

where $\Phi_{required}$ is the laser power needed at the ion for the ion interaction. These equations can be solved to estimate the number of ions that can be simultaneously addressed.

FIG. 2 illustrates a portion of a cell 202 of an apparatus for single ion addressing in accordance with one or more embodiments of the present disclosure. Cell 202 can be, for example, single cell 102 of apparatus 100 previously described in connection with FIG. 1.

As shown in FIG. 2, a laser (e.g., laser beam) from a fiber bundle (e.g., fiber bundle 110 previously described in connection with FIG. 1) can enter (e.g., be input into) cell 202. For example, the fiber bundle may split the laser into a plurality of components (e.g., fibers) before the laser enters cell 202, and only a single component of the laser (e.g., fiber 112-3 previously described in connection with FIG. 1) may enter cell 202, as previously described herein (e.g., in connection with FIG. 1).

The laser (e.g., laser component) may be, for example, a Doppler cooling laser or a quantum operation laser (e.g., a 369 nm Doppler cooling or quantum operation laser), as previously described herein (e.g., in connection with FIG. 1). However, embodiments of the present disclosure are not limited to a particular type of laser.

As shown in FIG. 2, cell 202 can include an electro-optic modulator 222. In embodiments in which the laser (e.g., laser component) is a Doppler cooling laser, electro-optic modulator 222 can be a 7.37 GHz electro-optic modulator, and in embodiments in which the laser is a quantum operation laser, electro-optic modulator 222 can be a 2.1 GHz electro-optic modulator. However, embodiments of the present disclosure are not limited to a particular type of electro-optic modulator.

Electro-optic modulator 222 can prepare the state of the laser (e.g., the state of the laser component). For example, electro-optic modulator 222 can generate large spacing sidebands for the state preparation, and address hyperfine transitions.

As shown in FIG. 2, cell 202 can include an acousto-optic modulator 224. Acousto-optic modulator 224 can be 200 MHz acousto-optic modulator. However, embodiments of the present disclosure are not limited to a particular type of acousto-optic modulator.

Acousto-optic modulator 224 can set the frequency and intensity of the laser and shutter the laser (e.g., set the frequency and intensity of and shutter the component of the laser) after electro-optic modulator 222 prepares the state of the laser. Light leakage from acousto-optic modulator 224 (e,g, from the shutter of the acousto-optic modulator) can be controlled using a radio-frequency (RF) switch (not shown in FIGS. 2A and 2B).

As shown in FIG. 2, cell 202 can include a Pockels cell 226 (e.g., a voltage-controlled wave plate). Pockels cell 226 can set the polarization of the laser (e.g., the polarization of the laser component) after acousto-optic modulator 224 sets the frequency and intensity of the laser and shutters the laser. For instance, Pockels cell 226 can be used to prevent electro-optic modulator 222 and/or acousto-optic modulator 224 from disturbing the polarization state of the laser by placing it after the other two devices.

As shown in FIG. 2, cell 202 can include a lens 232. Lens 232 can be, for example, a ball lens. Further, the focal length of lens 232 can be set to garner a particular beam waist and location for a given ion operation.

As shown in FIG. 2, lens 232 can focus the laser (e.g., the laser component), and direct the laser at mirror 234. Mirror 234 can be formed (e.g., placed) on the surface of a chip (e.g., die) (not shown in FIG. 2) that is not a part of (e.g., external to) cell 202. The distance between the center of lens 232 and the surface of the chip can be, for example, three millimeters (mm).

As shown in FIG. 2, mirror 234 can direct (e.g., reflect) the focused laser (e.g., the focused laser component) at ion 236 trapped in ion trap 238 such that ion 236 is illuminated by the focused laser. Ion trap 238 can be formed on the surface of a chip (not shown in FIG. 2), such as, for instance, the chip on which mirror 234 is formed, that is not a part of cell 202. The distance between mirror 234 and ion 236 can be, for example, 2.5 mm. Ion 236 can be, for example, a Yb ion. However, embodiments of the present disclosure are not limited to a particular type of ion.

Ion 236 may fluoresce (e.g., emit) light and/or perform a quantum operation when illuminated by the focused laser (e.g., by the focused laser component). The fluoresced light can be received (e.g., coupled) by lens 240 of cell 202, as illustrated in FIG. 2. Lens 240 can be, for example, a ball lens having a diameter of 2 mm. Further, the focal length of lens 240 can be set to couple the fluoresced light into an array of photo-multiplier tubes (e.g., array 242).

As shown in FIG. 2, cell 202 can include an array of photo-multiplier tubes 242. Photo-multiplier tube array 242 can detect (e.g., measure) the light (e.g., photons) fluoresced from ion 236. Photo-multiplier tubes may also be external to the entire apparatus (e.g., beyond fiber bundle 114 described in connection with FIG. 1).

Information (e.g., data) about the detected light can exit cell 202 and travel to additional electronics, such as, for instance, a charged-coupled device (CCD) or other detection device, through a fiber bundle (e.g., fiber bundle 114 previously described in connection with FIG. 1). For example, the information can be converted to electronic signals by photo-multiplier tube array 242, and the electronic signals can be output from cell 202, and travel to the fiber bundle and on to the additional electronics, through a fiber (e.g., fiber 116-1 previously described in connection with FIG. 1), as previously described herein (e.g., in connection with FIG. 1).

Although not shown in FIG. 2, cell 202 may include an additional mirror formed on the surface of the chip that can direct (e.g., reflect) the focused laser (e.g., the focused laser component) at a beam dump of cell 202 (not shown in FIG. 2) after the focused laser is aligned to (e.g., focused at), and illuminates, ion 236. The laser can then terminate at (e.g., upon reaching) the beam dump. Terminating the laser at the beam dump can mitigate stray light and/or heating in cell 202.

Cell 202 may be designed as a unit cell that can be repeated across an array (e.g., a 2D array) of ion traps formed on the chip and/or repeated a number of times with single cell 102 previously described in connection with FIG. 1. That is, the embodiment illustrated in FIG. 2 can be repeated across an array of ion traps formed on the chip. However, only one cell 202 has been shown in FIG. 2 for clarity and so as not to obscure embodiments of the present disclosure.

Although specific embodiments have been illustrated and described herein, those of ordinary skill in the art will appreciate that any arrangement calculated to achieve the same techniques can be substituted for the specific embodiments shown. This disclosure is intended to cover any and all adaptations or variations of various embodiments of the disclosure.

It is to be understood that the above description has been made in an illustrative fashion, and not a restrictive one. Combination of the above embodiments, and other embodiments not specifically described herein will be apparent to those of skill in the art upon reviewing the above description.

The scope of the various embodiments of the disclosure includes any other applications in which the above structures and methods are used. Therefore, the scope of various embodiments of the disclosure should be determined with reference to the appended claims, along with the full range of equivalents to which such claims are entitled.

In the foregoing Detailed Description, various features are grouped together in example embodiments illustrated in the figures for the purpose of streamlining the disclosure. This method of disclosure is not to be interpreted as reflecting an intention that the embodiments of the disclosure require more features than are expressly recited in each claim.

Rather, as the following claims reflect, inventive subject matter lies in less than all features of a single disclosed embodiment. Thus, the following claims are hereby incorporated into the Detailed Description, with each claim standing on its own as a separate embodiment.

What is claimed:

1. An apparatus for single ion addressing, comprising:
   a single cell configured to:
   set a frequency, intensity, and a polarization of a laser beam emitted by a single laser;
   shutter the laser beam emitted by the single laser;
   align the shuttered laser beam emitted by the single laser to an ion in an ion trap such that the ion fluoresces light and/or performs a quantum operation when the ion is illuminated by the shuttered laser beam emitted by the single laser; and
   detect the light fluoresced from the ion when the ion is illuminated by the shuttered laser beam emitted by the single laser.

2. The apparatus of claim 1, wherein the single cell is completely inside a vacuum.

3. The apparatus of claim 1, wherein the single cell is partially inside a vacuum.

4. The apparatus of claim 1, wherein the single cell includes an electro-optic modulator configured to prepare a state of the laser beam emitted by the single laser.

5. The apparatus of claim 1, wherein the single cell includes:
   an acousto-optic modulator configured to set the frequency and intensity of the laser beam emitted by the single laser and shutter the laser beam emitted by the single laser; and
   a Pockels cell configured to set the polarization of the laser beam emitted by the single laser.

6. The apparatus of claim 1, wherein the single cell includes an array of photo-multiplier tubes configured to detect the light fluoresced from the ion when the ion is illuminated by the shuttered laser beam emitted by the single laser.

7. A method for single ion addressing, comprising:
   preparing a state of a laser beam emitted by a single laser using a single cell;
   shuttering the laser beam emitted by the single laser using the single cell;
   aligning the shuttered laser beam emitted by the single laser to an ion in an ion trap using the single cell such that the ion fluoresces light and/or performs a quantum operation when the ion is illuminated by the shuttered laser beam emitted by the single laser; and
   detecting the light fluoresced from the ion when the ion is illuminated by the shuttered laser beam emitted by the single laser using the single cell.

8. The method of claim 7, wherein aligning the shuttered laser beam emitted by the single laser to the ion in the ion trap using the single cell includes:
   focusing the shuttered laser beam emitted by the single laser and directing the shuttered laser beam emitted by the single laser at a mirror of the single cell using a lens of the single cell; and directing the shuttered laser beam emitted by the single laser at the ion in the ion trap using the mirror of the single cell.

9. The method of claim 7, wherein the method includes terminating the shuttered laser beam emitted by the single laser using the single cell after aligning the shuttered laser beam emitted by the single laser to the ion in the ion trap.

10. The method of claim 7, wherein the method includes splitting the laser beam emitted by the single laser into a plurality of components before preparing the state of the laser beam emitted by the single laser and shuttering the laser beam emitted by the single laser.

11. The method of claim 10, wherein:
preparing the state of the laser beam emitted by the single laser includes preparing the state of a single one of the plurality of components of the laser beam emitted by the single laser;
shuttering the laser beam emitted by the single laser includes shuttering the single one of the plurality of components of the laser beam emitted by the single laser; and
aligning the shuttered laser beam emitted by the single laser to the ion in the ion trap includes aligning the shuttered component of the laser beam emitted by the single laser.

12. The method of claim 7, wherein the single laser is a Doppler cooling laser.

13. The method of claim 7, wherein the single laser is a quantum operation laser.

14. An apparatus for single ion addressing, comprising:
a vacuum; and
a single cell inside the vacuum and configured to:
set a frequency and a polarization of a laser beam emitted by a single laser;
shutter the laser beam emitted by the single laser;
align the shuttered laser beam emitted by the single laser to an ion in an ion trap such that the ion fluoresces light and/or performs a quantum operation when the ion is illuminated by the shuttered laser beam emitted by the single laser; and
detect the light fluoresced from the ion when the ion is illuminated by the shuttered laser beam emitted by the single laser.

15. The apparatus of claim 14, wherein the single cell includes:
a first lens configured to focus the shuttered laser beam emitted by the single laser;
a mirror configured to direct the focused shuttered laser beam emitted by the single laser at the ion in the ion trap such that the ion fluoresces light when the ion is illuminated by the shuttered laser beam emitted by the single laser; and
a second lens configured to receive the light fluoresced from the ion when the ion is illuminated by the shuttered laser beam emitted by the single laser.

16. The apparatus of claim 15, wherein the single cell includes an additional mirror configured to direct the laser beam emitted by the single laser at a beam dump after the laser beam emitted by the single laser is focused at the ion in the ion trap.

17. The apparatus of claim 14, wherein:
the apparatus includes a fiber bundle configured to split the laser beam emitted by the single laser into a plurality of fibers before the laser beam emitted by the single laser enters the vacuum; and
a single one of the fibers enters the single cell.

18. The apparatus of claim 14, wherein the apparatus includes a single fiber exiting the single cell.

19. The apparatus of claim 18, wherein the apparatus includes a fiber bundle configured to bundle the single fiber with a number of other fibers.

20. The apparatus of claim 14, wherein the apparatus includes a plurality of fibers entering and exiting the single cell.

* * * * *